United States Patent
WasDyke

(10) Patent No.: US 7,575,584 B2
(45) Date of Patent: *Aug. 18, 2009

(54) INTRAVASCULAR FILTER WITH BIOABSORBABLE CENTERING ELEMENT

(75) Inventor: Joel M. WasDyke, Eden Prairie, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 778 days.

This patent is subject to a terminal disclaimer.

(21) Appl. No.: 11/153,131

(22) Filed: Jun. 15, 2005

(65) Prior Publication Data

US 2005/0234504 A1 Oct. 20, 2005

Related U.S. Application Data

(63) Continuation of application No. 10/716,213, filed on Nov. 18, 2003, now Pat. No. 6,972,025.

(51) Int. Cl.
*A61F 2/01* (2006.01)
(52) U.S. Cl. .................................. 606/200
(58) Field of Classification Search .............. 606/200; 623/1.11
See application file for complete search history.

(56) References Cited

U.S. PATENT DOCUMENTS

| | | | |
|---|---|---|---|
| 4,688,553 A | 8/1987 | Metals | |
| 4,727,873 A | 3/1988 | Mobin-Uddin | |
| 4,781,177 A | 11/1988 | Lebigot | |
| 4,817,600 A | 4/1989 | Herms et al. | |
| 5,059,205 A | 10/1991 | El-Nounou et al. | |
| 5,152,777 A | 10/1992 | Goldberg et al. | |
| 5,324,304 A | 6/1994 | Rasmussen | |
| 5,375,612 A | 12/1994 | Cottenceau et al. | |
| 5,709,704 A | 1/1998 | Nott et al. | |
| 5,746,767 A | 5/1998 | Smith | |
| 5,792,400 A | 8/1998 | Talja et al. | |
| 5,836,968 A | 11/1998 | Simon et al. | |
| 5,836,969 A | 11/1998 | Kim et al. | |
| 5,853,420 A | 12/1998 | Chevillon et al. | |
| 5,957,975 A | 9/1999 | Lafont et al. | |
| 5,980,564 A | 11/1999 | Stinson | |

(Continued)

FOREIGN PATENT DOCUMENTS

EP 1 153 581 A1 11/2001

(Continued)

OTHER PUBLICATIONS

Meta Biomed Co., Ltd. "Properties of Sutures", http://www.metabiomed.com/mnu-04_04.html, Jul. 2003, 4 pages.

*Primary Examiner*—Todd E Manahan
*Assistant Examiner*—Michael G Mendoza
(74) *Attorney, Agent, or Firm*—Crompton, Seager & Tufte LLC

(57) ABSTRACT

Bioabsorbable centering elements for use in centering an implantable intravascular device within a body vessel are disclosed. The bioabsorbable centering element may include a number of support members configured to self-expand and engage the wall of the vessel when deployed. The support members may be formed from a biodegradable material adapted to degrade in vivo within a pre-determined period of time.

27 Claims, 5 Drawing Sheets

U.S. PATENT DOCUMENTS

| | | |
|---|---|---|
| 6,007,558 A | 12/1999 | Ravenscroft et al. |
| 6,217,600 B1 | 4/2001 | DiMatteo |
| 6,231,589 B1 | 5/2001 | Wessman et al. |
| 6,245,103 B1 | 6/2001 | Stinson |
| 6,267,776 B1 | 7/2001 | O'Connell |
| 6,273,900 B1 | 8/2001 | Nott et al. |
| 6,355,058 B1 | 3/2002 | Pacetti et al. |
| 6,468,290 B1 | 10/2002 | Weldon et al. |
| 6,506,205 B2 | 1/2003 | Goldberg et al. |
| 6,517,559 B1 | 2/2003 | O'Connell |
| 6,582,447 B1 | 6/2003 | Patel et al. |
| 6,620,183 B2 | 9/2003 | DiMatteo |
| 6,641,605 B1 | 11/2003 | Stergiopulos |
| 2003/0040754 A1 | 2/2003 | Mitchell et al. |
| 2003/0139765 A1 | 7/2003 | Patel et al. |
| 2003/0153945 A1 | 8/2003 | Patel et al. |
| 2003/0163159 A1 | 8/2003 | Patel et al. |
| 2003/0176888 A1 | 9/2003 | O'Connell |
| 2003/0199918 A1 | 10/2003 | Patel et al. |
| 2003/0208227 A1 | 11/2003 | Thomas |

FOREIGN PATENT DOCUMENTS

| | | |
|---|---|---|
| WO | WO 02/11812 A1 | 2/2002 |

US 7,575,584 B2

INTRAVASCULAR FILTER WITH BIOABSORBABLE CENTERING ELEMENT

This application is a continuation application of U.S. application Ser. No. 10/716,213, filed Nov. 18, 2003 now U.S. Pat. No. 6,972,025.

FIELD OF THE INVENTION

The present invention relates generally to the field of medical devices. More specifically, the present invention pertains to intravascular filters implantable within a body vessel.

BACKGROUND OF THE INVENTION

Blood clot filters are typically used in conjunction with thrombolytic agents and anti-coagulants to treat pulmonary embolism occurring within a patient. These devices are generally implanted within a vessel such as the inferior vena cava, and function by capturing blood clots (emboli) contained in the blood stream before they can reach the lungs and cause permanent damage to the body. To filter emboli, many conventional blood clot filters utilize a number of independent filter legs coupled to an apical head that can be expanded within the body to form a conical-shaped surface that collects the emboli without disturbing the flow of blood. Once collected, a natural clot lysing process occurs within the body to dissolve the emboli collected by the filter.

Delivery of the blood clot filter within the body is generally accomplished via an introducer sheath percutaneously inserted through the femoral (groin) or jugular (neck) veins. Such introducer sheaths are generally tubular in shape, and include an inner lumen configured to transport the filter in a collapsed position through the body. Once transported to a desired location within the body, the filter can then be removed from wall. A needle, hook, barb, prong, wedge or other attachment means disposed on the base of each filter leg can be used to secure the filter within the vessel.

The efficacy of the filter to capture blood clots is dependent in part on the ability of the filter to properly center when withdrawn from within the introducer sheath. Tilting of the filter may result if the apical head is not aligned centrally within the vessel, causing the filter legs to asymmetrically engage the vessel wall. In certain circumstances, tilting of the filter may affect the ability of the device to effectively capture emboli contained in the blood. To overcome this problem, more recent designs in the art have focused on filters having the ability to self-center when placed in the body. These designs, while providing a means to center the filter within the vessel, typically add to the complexity and size of the filter and accompanying introducer sheath.

SUMMARY OF THE INVENTION

The present invention pertains to a bioabsorbable centering element for use in centering an intravascular filter within a vessel. A bioabsorbable centering element in accordance with an exemplary embodiment of the present invention may include a number of biodegradable support members configured to self-expand when withdrawn from within an introducer sheath and deployed in the body. Each support member may have a generally elongated shape with a first end coupled to the intravascular device or an optional biodegradable cap, and a second end that is biased to displace in an outward direction. Upon deployment, the support members expand in an outward direction and apply a force to the interior wall of the vessel, preventing the intravascular device from becoming off-centered or tilted within the vessel.

The bioabsorbable centering element may be formed from a biodegradable material configured to degrade in the body within a predetermined period of time. The time required for the material to degrade may depend on a number of intrinsic and extrinsic design factors including, for example, the structure and composition of the support members, and the particular biological environment in which the device is implanted. In certain embodiments, the support members can be configured to substantially degrade in vivo within a few days after implantation, allowing the bioabsorbable centering element to be functional during the initial period of implantation and for the days shortly thereafter when migration of the filter is most likely.

DETAILED DESCRIPTION OF THE INVENTION

The following description should be read with reference to the drawings, in which like elements in different drawings are numbered in like fashion. The drawings, which are not necessarily to scale, depict selected embodiments and are not intended to limit the scope of the invention. Although examples of construction, dimensions, and materials are illustrated for the various elements, those skilled in the art will recognize that many of the examples provided have suitable alternatives that may be utilized.

In at least some embodiments, the present invention is directed to a bioabsorbable centering element for use in centering an implantable intravascular filter within a body vessel. As will be described in greater detail below with respect to specific embodiments, the bioabsorbable centering element may include one or more biodegradable support members operatively coupled to the intravascular device and configured to self-expand and apply an outwardly directed force to the interior wall of the vessel. The biodegradable support members may be coupled to various locations of the intravascular device, and may be oriented in a manner that reduces interference with the other components of the device. Upon deployment within the body, the outwardly directed force exerted by the biodegradable support members on the interior of the vessel wall prevents the intravascular filter from becoming off-centered or tilted within the vessel. In addition, the biodegradable support members reduce the occurrence of downstream filter migration by applying a sufficient radial force to the vessel wall that resists longitudinal movement of the filter within the vessel.

Figure 1:
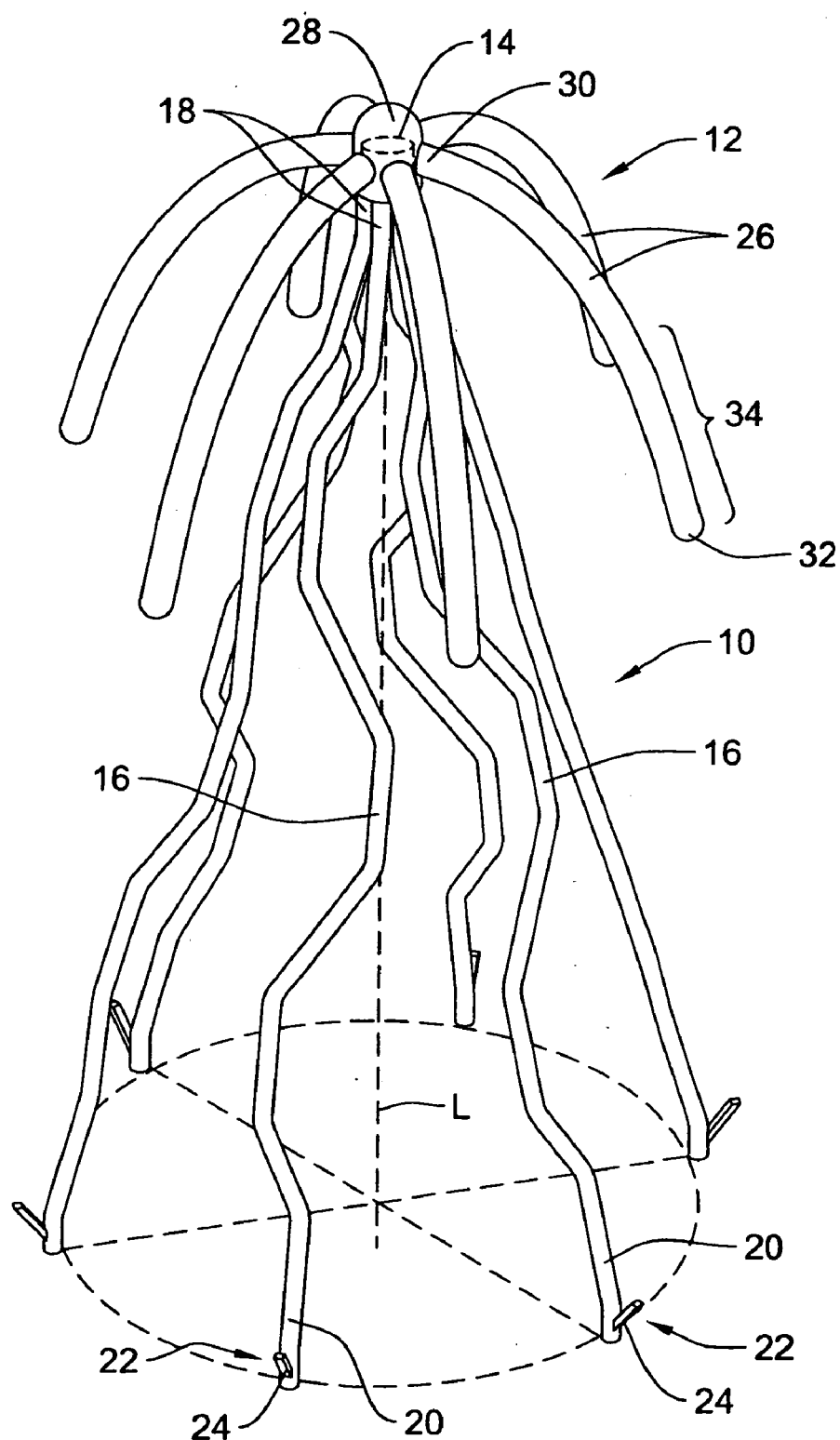
FIG. 1 is a perspective view of an intravascular filter employing a bioabsorbable centering element in accordance with an exemplary embodiment of the present invention.

FIG. 1 is a perspective view of an intravascular filter 10 employing a bioabsorbable centering element 12 in accordance with an exemplary embodiment of the present invention. Intravascular filter 10, illustratively a blood clot filter, includes an apical head 14 and a number of elongated filter legs 16 each having a proximal section 18 and a distal section 20. In the illustrative filter configuration depicted in FIG. 1, the filter legs 16 are shown having a shape and structure similar to that described in U.S. Pat. No. 5,059,205 to El-Nounou et al., which is incorporated herein by reference in its entirety. It should be understood, however, that the particular configuration of the filter may vary in size, shape, material composition, etc. without deviating from the scope of the invention.

As can be seen in FIG. 1, the apical head 14 of filter 10 defines a common longitudinal axis L about which the filter legs 16 are configured to radially expand when deployed in the body. The filter legs 16 can be arranged at equidistant intervals such that the filter legs 16 are radially spaced symmetrically about the longitudinal axis L. In the illustrative filter 10 depicted in FIG. 1, filter 10 includes six filter legs 16 that are arranged radially about the longitudinal axis L at equidistant 600 intervals. The number and specific arrangement of the filter legs 16 can, of course, vary depending on the particular mechanical characteristics desired in the filter 10. An intravascular filter in accordance with the present invention may include a greater or smaller number of filter legs than illustrated in FIG. 1, and may be arranged in either a symmetric or asymmetric manner.

The distal section 20 of each filter leg 16 may include an attachment section 22 configured to pierce and secure the filter 10 to the wall of the vessel. The attachment section 22 may include a hook 24 formed integrally with or coupled to the distal section 20 of the filter leg 16. The hook 24 may be hingedly connected to the filter leg 16 to permit the hook 24 to bend and assume a low profile when the filter 10 is loaded into an introducer sheath. Each hook 24 may taper distally to a pointed tip, which, when engaged in the vessel wall (see FIG. 5), forms a small pin point lesion in the endothelium layer of the vessel. Although a hook 24 is specifically illustrated in FIG. 1, it should be understood that attachment section 22 may employ other means for piercing the vessel wall. For example, a needle, barb, prong, wedge or other suitable attachment means can be utilized in lieu of, or in addition to, the hooks 24 illustrated in FIG. 1.

The elongated filter legs 16 may be formed at least in part of a radiopaque material configured to permit monitoring of the filter 10 within the body using a fluoroscope. Radiopaque materials are understood to be materials capable of producing a relatively bright image on a fluoroscopic monitor or other imaging device. In use, the bright image produced by the material allows the physician to visualize the filter to determine its location and/or deployment status within the vessel. Examples of suitable radiopaque materials may include gold, palladium, platinum, tungsten, and stainless steel. Polymeric materials loaded with a radiopaque filler such as barium sulfate ($BaSO_4$) or bismuth subcarbonate ($(BiO)_2CO_3$) may also be employed, if desired.

In certain embodiments, the filter legs 16 may be formed from a composite material configured to exhibit certain desirable characteristics within the body such as high elasticity and radiopacity. For example, one or more of the filter legs 16 may be formed from a composite material comprising a superelastic alloy such as nickel-titanium (Nitinol), and a relatively radiopaque material such as stainless steel or platinum. The use of such composite materials allows the filter to be collapsed into smaller introducer sheaths without permanently deforming the filter legs 16.

The bioabsorbable centering element 12 may include a number of biodegradable support members 26 extending outwardly from a biodegradable cap 28 disposed about the apical head 14 of the filter 10. The biodegradable support members 26 and biodegradable cap 28 may be formed either as separate elements that are attached together, or as a single member using, for example, an injection molding process. As is described in greater detail below with respect to FIGS. 3-5, the biodegradable support members 26 are configured to extend outwardly to engage the vessel wall and center the filter 10 within the vessel.

In the exemplary embodiment illustrated in FIG. 1, each support member 26 has a generally elongated shape with a substantially circular cross-section. A first end 30 of the support member 26 is attached to or formed integrally with the biodegradable cap 28. A second, peripheral end 32 of the support member 26, in turn, is unconstrained relative to the biodegradable cap 28, allowing the support member 26 to displace in an outward direction.

In a fully expanded position illustrated in FIG. 1, each biodegradable support member 26 extends outwardly away from the longitudinal axis L of the filter 10. When collapsed within an introducer sheath, the biodegradable support members 26 compress inwardly towards the longitudinal axis L. This compression inwardly serves to bias the support members 26 in an outward direction, causing them to self-expand and return to their original (i.e. expanded) orientation when deployed in the vessel. The orientation at which the support member 26 diverges may be varied to alter the profile and mechanical characteristics of the bioabsorbable centering element 12. Other factors such as the length and thickness of the support members 26 may also be altered to impart a particular mechanical characteristic to the device.

In certain embodiments, each support member 26 may have a bowed or arcuate shape along its length, orienting a peripheral portion 34 of the support member 26 in a direction substantially parallel to the vessel wall. In use, this bowed or arcuate shape prevents the support members 26 from distending or piercing the vessel wall.

Figure 2:
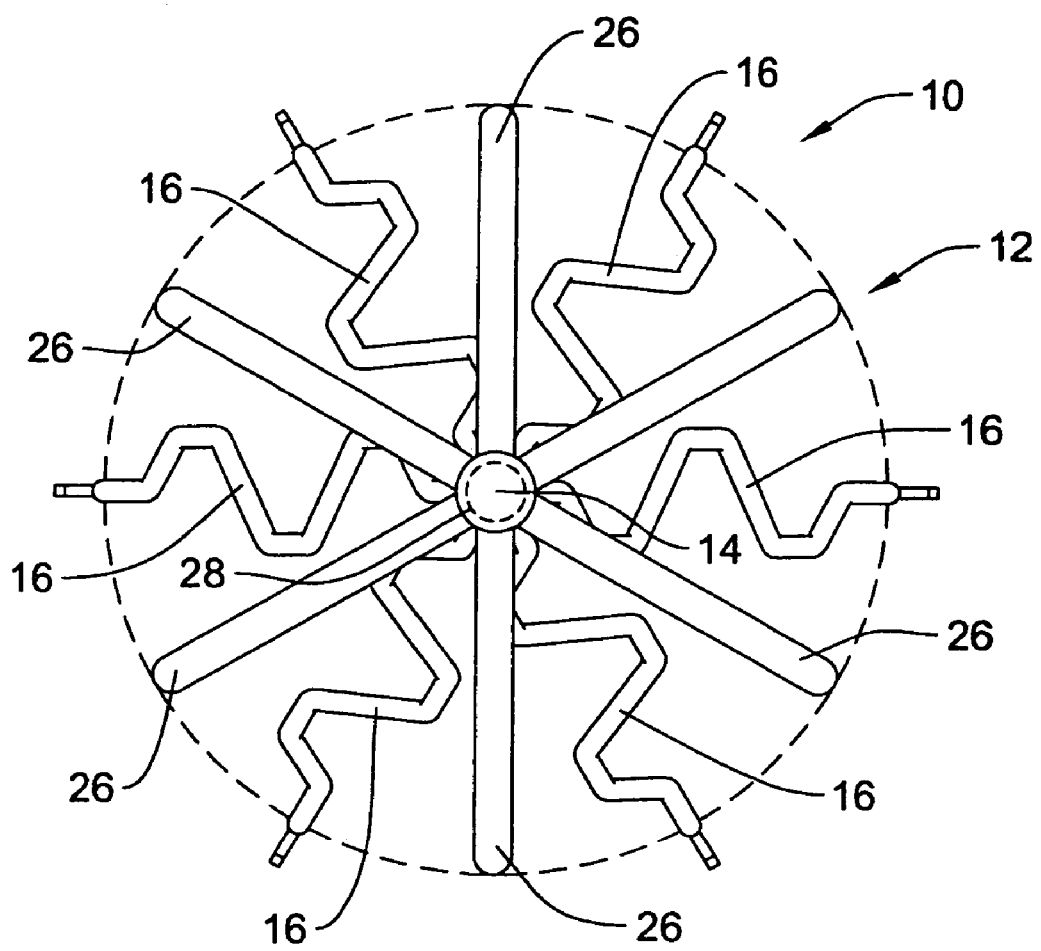
FIG. 2 is a top perspective view of the intravascular filter and bioabsorbable centering element illustrated in FIG. 1.

FIG. 2 is a top perspective view of the filter 10 and bioabsorbable centering element 28 of FIG. 1. As can be seen in FIG. 2, the bioabsorbable centering element 12 may include six biodegradable support members 26 each disposed at equidistant intervals (i.e. 60°) with respect to each other. The number and arrangement of the support members 26 may be varied to alter the mechanical characteristics of the centering element 28 within the body. For example, while the exemplary embodiment illustrated in FIGS. 1-2 shows each of the six support members 26 radially offset from each radially adjacent filter leg 16 by approximately 30° intervals, other embodiments having radially aligned or offset intervals are possible.

Each support member 26 may be formed from a suitable biocompatible material configured to degrade within the body within a predetermined period of time. While a variety of materials are capable of degrading within the body, a biodegradable material in accordance with the present invention is understood to be one that is capable of degradation in vivo within a few days up to a number of years. Examples of suitable biodegradable materials may include, but are not limited to, polylactic acid (PLA), polyglycolic acid (PGA), copolymer poly(lactide-co-glycolide) (PLGA), polydioxanone, polyanhydrides, trimethylene carbondate, poly(hydroxybutyrate), poly(g-ethyl glutamate), poly(ortho esters), polycyanoacrylate, polyphosphazenes, poly(a-hydroxy acids), poly(e-caprolactone), polysaccharides (e.g. cellulose, chitin, dextran), modified proteins (e.g. fibrin, casein), albumin, collagen, gelatin, alginate, starch, and/or copolymers, mixtures or combinations thereof.

The degradation time of the material will vary depending in part on the type of material employed. To permit the bioabsorbable centering element 12 to function during the initial period of implantation, and for the days shortly thereafter when migration of the filter 10 within the vessel is most likely, a degradation time lasting approximately 20-30 days is generally sufficient. In certain embodiments, however, quicker degradation times of about 3 to 5 days may be desirable.

The period of time that the bioabsorbable centering element 12 remains functional within the vessel is dependent in part upon a number of intrinsic and extrinsic design factors. Intrinsic factors such as the absorption rate of the material(s) employed and the specific geometry of the support members 26 may affect the period of time necessary for the bioabsorbable centering element 12 to degrade in the body. Factors unique to the biodegradable material such as the level of crystallinity, orientation, substituents and molecular weight, for example, may have an impact on the period of time required for the material to degrade in vivo. Extrinsic factors such as the pH of the biological medium, electrolytes, external stress, temperature, radiation, free radicals, and enzymes may also affect the degradation time of the support members 26 in vivo. Other environmental factors such as material processing, sterilization, and storage may affect the degradation time of the support members 26.

Based on a given set of extrinsic and intrinsic conditions, a specific absorption rate may be designed by utilizing materials with either a fast degradation rate or a slow degradation rate. For example, biodegradable materials having a relatively low molecular weight can be employed to increase the rate at which the support members 26 degrade within the body. Mechanical properties such as tensile strength and bendability may also be altered by selecting materials having a particular level of crystallinity or other intrinsic characteristic.

The degradation of absorbable polymers is due primarily to hydrolysis. A hydrolytic reaction causes the molecular chains of the polymer to break down and the chain length to decrease. This process results in a reduction in the physical and mechanical properties of the material over time. A loss of mass occurs when a significant number of chains are broken to allow diffusion of small molecular chains out of the polymer and into the environment. Disintegration of the polymer finally occurs when there has been a loss in strength and mass, and portions of the polymer become detached. With certain materials, this hydrolytic reaction forms by-products that can be easily metabolized and/or excreted within the body. With bioabsorbable PGA or PLLA, for example, a hydrolytic chain scission occurs within the body to produce lactic and glycolic acid. These acids are then metabolized by the surrounding tissue and fluids and converted (via a citrate cycle) into carbon dioxide ($CO_2$) that can be easily eliminated from the body via respiration.

Degradation of absorbable polymers tends to be non-homogeneous since such materials are generally semi-crystalline in structure, and thus exhibit both amorphous and crystalline regions. Since degradation occurs more rapidly at the amorphous regions rather than at the crystalline regions, a decrease in tensile strength in the support members 26 generally occurs prior to a decrease in mass. This loss in tensile strength occurs prior to the loss of mass since the support members 26 degrade through their bulk (i.e. in an inside-out manner) rather than from surface erosion.

Figure 3:
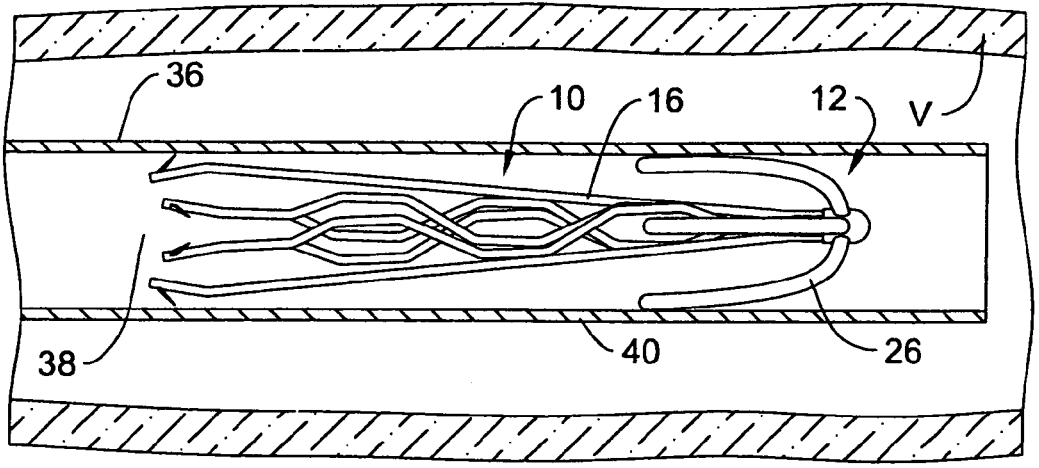
FIG. 3 is a partial cross-sectional view of the intravascular filter of FIG. 1, showing the filter and bioabsorbable centering element loaded into an introducer sheath and advanced to a target region within a body vessel.

FIG. 3 is a partial cross-sectional view of the intravascular filter 10 of FIG. 1, showing the filter 10 and bioabsorbable centering element 12 loaded into a delivery device 36 and advanced to a target region within a body vessel V. Delivery device 36, illustratively an introducer sheath, includes an inner lumen 38 configured to contain the filter 10 and bioabsorbable centering element 12 in a collapsed position therein. The filter 10 and bioabsorbable centering element 12 can be positioned within a distal section 40 of the delivery device 36 for insertion via a femoral approach (as shown in FIG. 3), or can be loaded into the distal section 40 of the delivery device 36 in an inverted manner (i.e. left to right), allowing the filter 10 to be inserted via a jugular approach.

Figure 4:
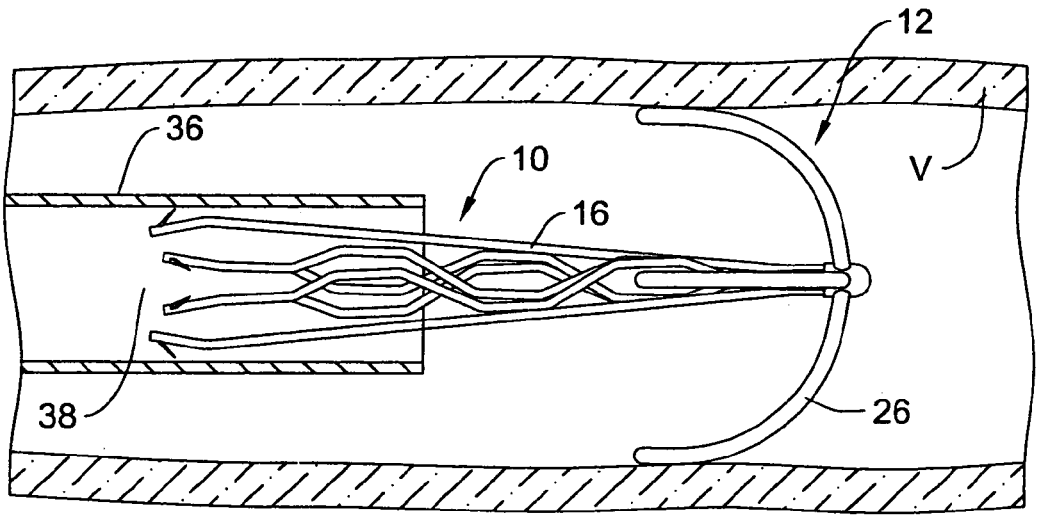
FIG. 4 is another partial cross-sectional view of the intravascular filter of FIG. 1, showing the initial deployment of the filter and the bioabsorbable centering element within the vessel.

FIG. 4 is a partial cross-sectional view showing the initial deployment of the filter 10 and bioabsorbable centering element 12 within the vessel V. As can be seen in FIG. 4, the biodegradable support members 26 are configured to self-expand outwardly away from the center of the filter 10 when withdrawn from the delivery device 36. The ability of the filter 10 to self-center upon insertion allows the device to be inserted in a wide range of lumen configurations using different placement techniques. As the filter 10 is withdrawn, the peripheral portion 32 of each support member 26 engages the interior wall of the vessel V, imparting a force thereto that prevents the filter 10 from becoming off-centered or tilted within the vessel V.

Figure 5:
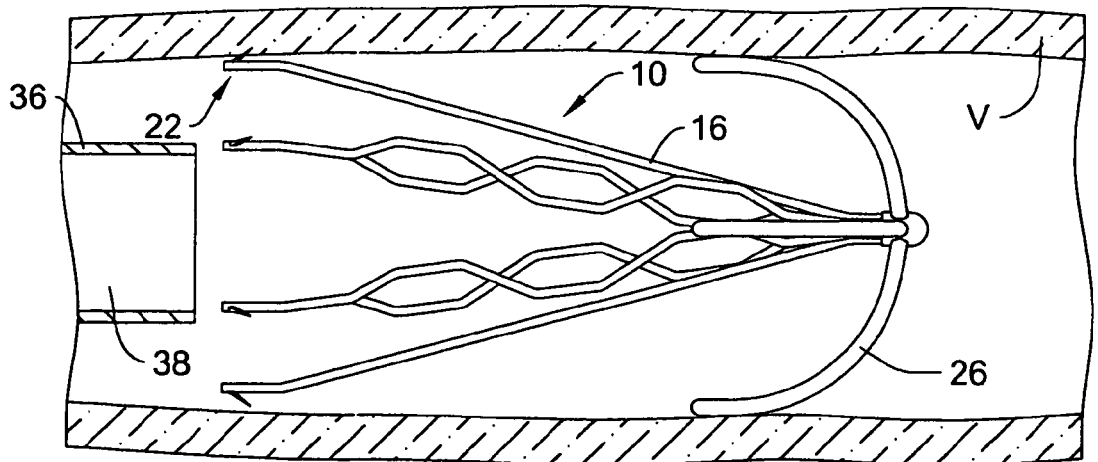
FIG. 5 is another partial cross-sectional view of the intravascular filter of FIG. 1, showing the filter and bioabsorbable centering element after implantation within the vessel.

Continued withdrawal of the filter 10 from within the delivery device 36 causes the attachment section 22 on each filter leg 16 to become unconstrained within the inner lumen 38 and spring open, thereby securing the filter 10 to the vessel wall, as shown in FIG. 5. After initial deployment within the body, exposure of the support members 26 to various fluids and tissue causes the support members 26 to decompose and become absorbed within the body leaving only the centered filter 10 within the vessel V.

Figure 6:
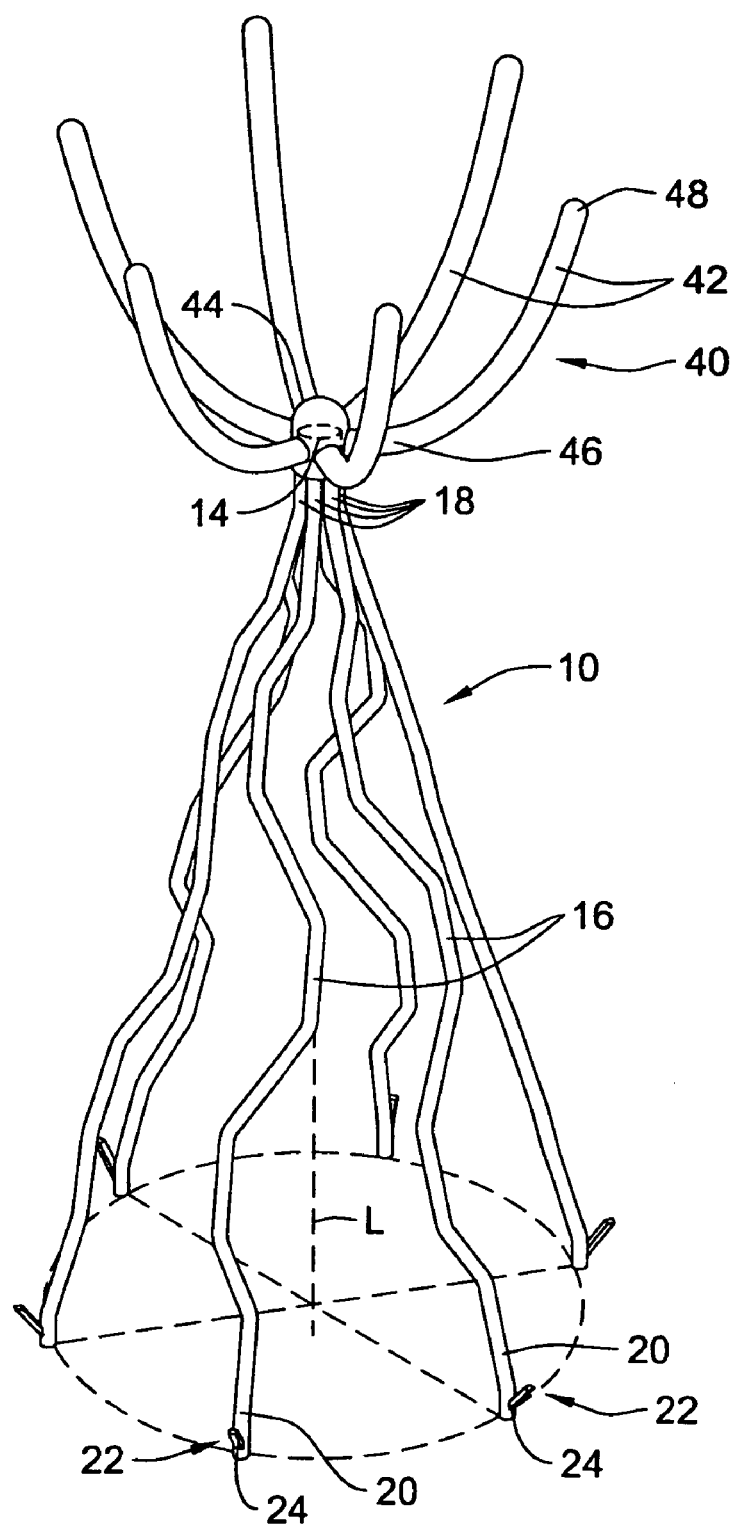
FIG. 6 is a perspective view of an intravascular filter employing a bioabsorbable centering element in accordance with another exemplary embodiment of the present invention.

FIG. 6 is a perspective view of a bioabsorbable centering element 40 in accordance with another exemplary embodiment of the present invention having a number of biodegradable support members 42 oriented in a direction opposite that depicted in FIGS. 1-2. As shown in FIG. 6, each support member 42 may extend from a biodegradable cap 44 disposed about the apical head 14 of the filter 10. The biodegradable support members 42 and biodegradable cap 44 may be formed either as separate elements that are attached together, or as a single member using, for example, an injection molding process.

Each biodegradable support member 42 may have a generally elongated shape with a substantially circular cross-section. A first, basal end 46 of the support member 42 may be secured to the biodegradable cap 44. The second, peripheral end 48 of the support member 42, in turn, is unconstrained, allowing the peripheral end 48 to displace in an outward direction and engage the vessel wall. Each support member 42 may have a bowed or arcuate shape along its length that may be used to prevent piercing and distension from occurring within the vessel as the bioabsorbable centering element 40 is deployed.

When collapsed, the filter 10 and attached bioabsorbable centering element 40 assume a longer length but smaller profile, allowing the filter 10 to be loaded into smaller sized introducer sheaths. Moreover, since the support members 42 are oriented away from base of the filter 10 and filter legs 16, entanglement of the support members 42 with the filter legs 16 is further reduced.

Figure 7:
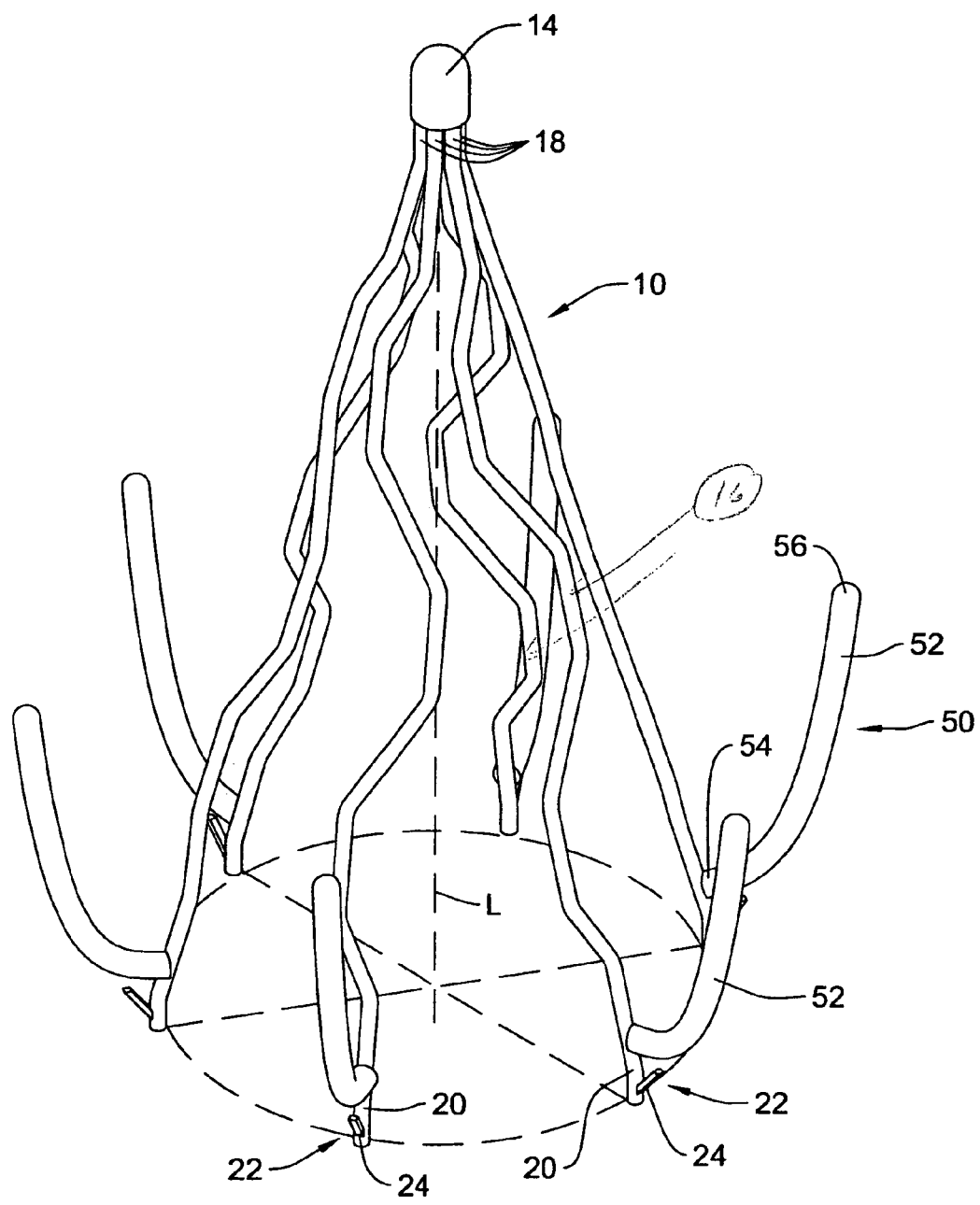
FIG. 7 is a perspective view of an intravascular filter employing a bioabsorbable centering element in accordance with another exemplary embodiment of the present invention.

FIG. 7 is a perspective view of a bioabsorbable centering element 50 in accordance with another exemplary embodiment of the present invention employing a number of biodegradable support members 52 attached to the base of the filter 10. Each biodegradable support member 52 may have a generally elongated shape with a substantially circular cross-section. A first, basal end 54 of the support member 52 may be secured to the distal section 20 of the filter leg 16 at or near the base of the filter 10. The second, peripheral end 56 of the support member 52, in turn, is unconstrained relative to the filter leg 16, allowing it to displace in an outward direction and engage the vessel wall. Each support member 52 may have a bowed or arcuate shape along its length, which, as discussed herein, may be used to prevent piercing and distension from occurring within the vessel as the bioabsorbable centering element 50 is deployed.

The bioabsorbable centering element 50 functions in a manner similar to that described above with respect to bioabsorbable centering elements 12 and 40. For example, the biodegradable support members 52 may be configured to spring open when deployed from within an introducer sheath, imparting a force to the interior wall of the vessel that resists tilting of the filter 10. As with other embodiments described herein, the support members 52 can be configured to function for a pre-determined period of time (e.g. 20-30 days) before disintegrating within the body.

While the embodiments specifically depicted herein illustrate the use of a bioabsorbable centering element in conjunction with intravascular filters, and more specifically blood clot filters, it will be readily apparent that the invention may be applicable to a variety of other intravascular devices implantable within the body. For example, certain aspects of the present invention may be applicable to embolic protection filters, retrieval baskets, laparoscopic devices, endoscopic devices, snares, stents, or other implantable medical devices wherein centering within a vessel may be desired.

Having thus described the several embodiments of the present invention, those of skill in the art will readily appreciate that other embodiments may be made and used which fall within the scope of the claims attached hereto. Numerous advantages of the invention covered by this document have been set forth in the foregoing description. It will be understood that this disclosure is, in many respects, only illustrative. Changes may be made in details, particularly in matters of shape, size and arrangement of parts without exceeding the scope of the invention.

What is claimed is:

1. An intravascular filter, comprising:
   an apical head;
   a plurality of filter legs each having a proximal section and a distal section, the proximal section of each filter leg being secured to the apical head, the distal section having a distal end, the plurality of distal ends defining a base;
   a plurality of biodegradable support members each having a first end and a second end, the first end of each biodegradable support member being secured to a biodegradable cap, the second end of each biodegradable support member biased to radially expand outwardly within a body vessel; and
   wherein the biodegradable support members are generally oriented in a direction away from said base.

2. The intravascular filter of claim 1, wherein the biodegradable cap is coupled to the apical head.

3. The intravascular filter of claim 1, wherein each of the plurality of biodegradable support members is radially offset from each of the plurality of filter legs.

4. The intravascular filter of claim 1, wherein said plurality of biodegradable support members form a bioabsorbable centering element having a first state prior to bioabsorption configured to exert an outwardly directed force on the wall of the body vessel, and a second state subsequent to bioabsorption configured to not exert the outwardly directed force.

5. The intravascular filter of claim 4, wherein the bioabsorbable centering element is configured to degrade in vivo in about 20 to 30 days.

6. The intravascular filter of claim 4, wherein the bioabsorbable centering element is configured to degrade in vivo in about 3 to 5 days.

7. The intravascular filter of claim 1, wherein each biodegradable support member has an elongated shape with a substantially circular cross-section.

8. The intravascular filter of claim 7, wherein each biodegradable support member has a bowed or arcuate shape along its length.

9. The intravascular filter of claim 1, wherein the biodegradable support members include a biodegradable material selected from the group consisting of polylactic acid, polyglycolic acid, copolymer poly(lactide-co-glycolide), polydioxanone, polyanhydrides, trimethylene carbondate, poly(hydroxybutyrate), poly(g-ethyl glutamate), poly(ortho esters), polycyanoacrylate, polyphosphazenes, poly(a-hydroxy acids), poly(e-caprolactone), polysaceharides, modified proteins, albumin, collagen, gelatin, alginate, and starch.

10. The intravascular filter of claim 1, wherein the intravascular filter is adapted to self-center upon insertion within the body vessel.

11. An intravascular filter, comprising:
    an apical head;
    a plurality of filter legs each having a proximal section and a distal section, the proximal section of each filter leg being secured to the apical head, the distal section having a distal end, the plurality of distal ends defining a base; and
    a bioabsorbable centering element for centering the intravascular filter within a body vessel, the centering element including a plurality of biodegradable support members each having a constrained end and a free end, the constrained end of each biodegradable support member being secured to a biodegradable cap coupled to the apical head, the free end of each biodegradable support member biased to radially expand outwardly within a body vessel.

12. The intravascular filter of claim 11, wherein each of the plurality of biodegradable support members is radially offset from each of the plurality of filter legs.

13. The intravascular filter of claim 11, wherein said plurality of biodegradable support members form a bioabsorbable centering element having a first state prior to bioabsorption configured to exert an outwardly directed force on the wall of the body vessel, and a second state subsequent to bioabsorption configured to not exert the outwardly directed force.

14. The intravascular filter of claim 11, wherein the bioabsorbable centering element is configured to degrade in vivo in about 20 to 30 days.

15. The intravascular filter of claim 11, wherein the bioabsorbable centering element is configured to degrade in vivo in about 3 to 5 days.

16. The intravascular filter of claim 11, wherein each biodegradable support member has an elongated shape with a substantially circular cross-section.

17. The intravascular filter of claim 16, wherein each biodegradable support member has a bowed or arcuate shape along its length.

18. The intravascular filter of claim 1, wherein the biodegradable support members include a biodegradable material selected from the group consisting of polylactic acid, polyglycolic acid, copolymer poly(lactide-co-glycolide), polydioxanone, polyanhydrides, trimethylene carbondate, poly(hydroxybutyrate), poly(g-ethyl glutamate), poly(ortho esters), polycyanoacrylate, polyphosphazenes, poly(a-hydroxy acids), poly(e-caprolactone), polysaccharides, modified proteins, albumin, collagen, gelatin, alginate, and starch.

19. An intravascular filter, comprising:
an apical head;
a plurality of filter legs each having a proximal section and a distal section, the proximal section of each filter leg being secured to the apical head, the distal section having a distal end, the plurality of distal ends defining a base;
a plurality of biodegradable support members each having a first end and a second end, the first end of each biodegradable support member being secured to a biodegradable cap, the second end of each biodegradable support member biased to radially expand outwardly within a body vessel; and
wherein each of the plurality of biodegradable support members is radially offset from each of the plurality of filter legs.

20. The intravascular filter of claim 19, wherein the biodegradable cap is coupled to the apical head.

21. The intravascular filter of claim 19, wherein said plurality of biodegradable support members form a bioabsorbable centering element having a first state prior to bioabsorption configured to exert an outwardly directed force on the wall of the body vessel, and a second state subsequent to bioabsorption configured to not exert the outwardly directed force.

22. The intravascular filter of claim 21, wherein the bioabsorbable centering element is configured to degrade in vivo in about 20 to 30 days.

23. The intravascular filter of claim 21, wherein the bioabsorbable centering element is configured to degrade in vivo in about 3 to 5 days.

24. The intravascular filter of claim 19, wherein each biodegradable support member has an elongated shape with a substantially circular cross-section.

25. The intravascular filter of claim 24, wherein each biodegradable support member has a bowed or arcuate shape along its length.

26. The intravascular filter of claim 19, wherein the biodegradable support members include a biodegradable material selected from the group consisting of polylactic acid, polyglycolic acid, copolymer poly(lactide-co-glycolide), polydioxanone, polyanhydrides, trimethylene carbondate, poly(hydroxybutyrate), poly(g-ethyl glutamate), poly(ortho esters), polycyanoacrylate, polyphosphazenes, poly(a-hydroxy acids), poly(e-caprolactone), polysaccharides, modified proteins, albumin, collagen, gelatin, alginate, and starch.

27. The intravascular filter of claim 19, wherein the intravascular filter is adapted to self-center upon insertion within the body vessel.

\* \* \* \* \*